US012208195B2

(12) United States Patent
Illes Csok

(10) Patent No.: US 12,208,195 B2
(45) Date of Patent: Jan. 28, 2025

(54) DEVICE FOR REMOVING BY SUCTION A BODILY FLUID, PRIMARILY NASAL FLUID

(71) Applicant: ILLÉS CSÓK ÉS TÁRSA KFT, Budapest (HU)

(72) Inventor: Anna Illes Csok, Budapest (HU)

(73) Assignee: ILLES CSOK ES TARSA KFT, Budapest (HU)

( * ) Notice: Subject to any disclaimer, the term of this patent is extended or adjusted under 35 U.S.C. 154(b) by 174 days.

(21) Appl. No.: 17/872,377

(22) Filed: Jul. 25, 2022

(65) Prior Publication Data
US 2022/0355016 A1 Nov. 10, 2022

Related U.S. Application Data

(63) Continuation-in-part of application No. 16/966,639, filed as application No. PCT/HU2019/000001 on Jan. 11, 2019, now abandoned.

(30) Foreign Application Priority Data

Jan. 31, 2018 (HU) .................................. P1800039

(51) Int. Cl.
A61M 1/00 (2006.01)
A47L 9/28 (2006.01)

(52) U.S. Cl.
CPC ........... *A61M 1/682* (2021.05); *A47L 9/2805* (2013.01); *A61M 1/63* (2021.05); *A61M 1/69* (2021.05); *A61M 1/71* (2021.05); *A61M 1/78* (2021.05); *A61M 1/84* (2021.05); *A61M 1/86* (2021.05); *A61M 2210/0618* (2013.01)

(58) Field of Classification Search
CPC .......... A61M 1/68; A61M 1/682; A61M 1/63; A61M 1/84; A61M 1/69; A61M 1/71; A61M 1/78; A61M 1/86; A61M 2210/0418; A61L 9/2805
See application file for complete search history.

(56) References Cited

U.S. PATENT DOCUMENTS

| 5,800,425 | A | * | 9/1998 | DeLeonardis | .......... | A61M 1/79 604/27 |
| 8,827,945 | B2 | * | 9/2014 | Baker | ..................... | A61M 1/72 604/35 |
| 9,649,414 | B2 | | 5/2017 | Streitmann et al. | | |

(Continued)

FOREIGN PATENT DOCUMENTS

| EP | 0752893 B1 | 1/1997 |
| FR | 2728469 A1 | 6/1996 |

(Continued)

OTHER PUBLICATIONS

Translation of RU 87083 U1 (Year: 2007).*
Translation of WO 94/25083 (Year: 1994).*

*Primary Examiner* — Philip R Wiest
(74) *Attorney, Agent, or Firm* — Olson & Cepuritis, Ltd.

(57) ABSTRACT

A device for removal of a body fluid, such as a nasal fluid, and includes a collector vessel that traps and collects body fluid entrained in an air stream passing through the collector vessel. The collector vessel is made up of first and second bell shaped shell portions removably attached to one another and holding therebetween an internal, removable central member that temporarily reverses the direction and reduces velocity of the air stream.

6 Claims, 2 Drawing Sheets

(56) References Cited

U.S. PATENT DOCUMENTS 9,993,584 B2 * 6/2018 Mehta ................. A61M 1/84
10,398,810 B2 * 9/2019 Goudy ................ A61M 1/682

FOREIGN PATENT DOCUMENTS

| FR | 2912062 A1 | 8/2008 | |
|---|---|---|---|
| HU | 215653 B | 1/1999 | |
| RU | 87083 U1 * | 12/2008 | |
| RU | 87082 U1 | 9/2009 | |
| WO | 199425083 A1 | 11/1994 | |
| WO | WO-9425083 A1 * | 11/1994 | .......... A61M 1/0023 |
| WO | 1999053819 A2 | 10/1999 | |
| WO | WO 99/53819 | * 10/1999 | |

* cited by examiner

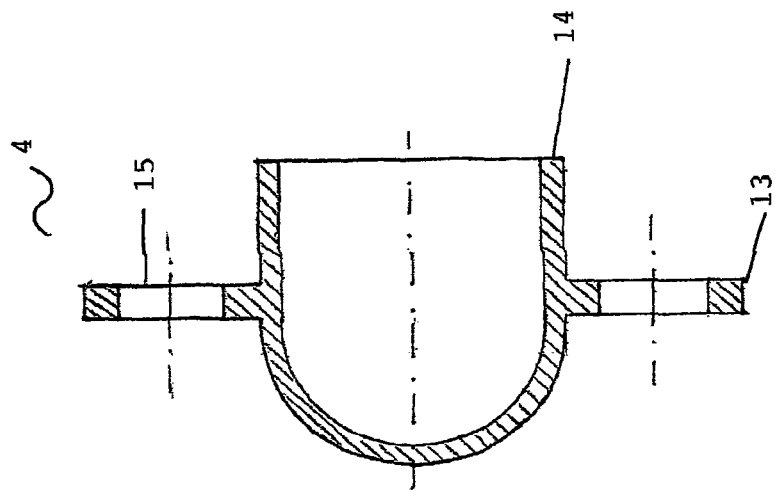
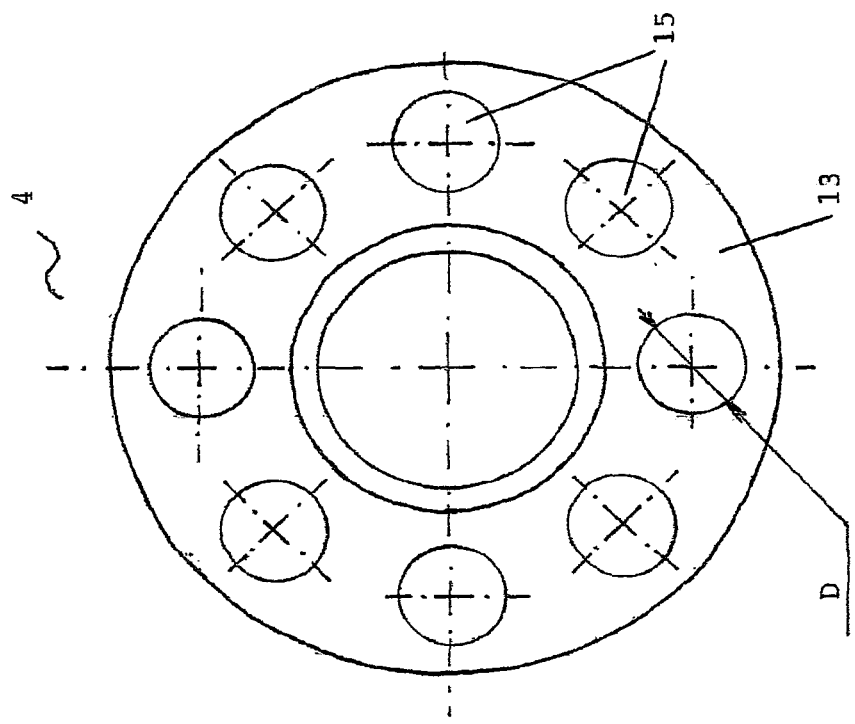

DEVICE FOR REMOVING BY SUCTION A BODILY FLUID, PRIMARILY NASAL FLUID

CROSS-REFERENCE TO RELATED APPLICATIONS

This application is a continuation-in-part of U.S. Ser. No. 16/966,639, filed Jul. 31, 2020 which, in turn, is a U.S. National Stage of PCT/HU2019/000001, filed Jan. 11, 2019, which claims priority of Hungarian Application No. P1800039, filed Jan. 31, 2018, each of which is incorporated herein by reference.

TECHNICAL FIELD OF THE INVENTION

The invention relates to a device for removing a body fluid, particularly nasal fluid, by applying a vacuum source.

BACKGROUND OF THE INVENTION

Different devices for removing unwanted exudates from the human body have been developed. An example of known devices for removing, by suction, nasal fluids is a pipette terminated by a rubber cap, wherein the fluid is removed by applying vacuum produced by manually compressing the rubber cap. A common drawback of these devices is that they are not capable of completely removing the exudate, and at the same time are either not suited for reuse or are difficult to sterilize so that reuse risks infection.

To address this problem, Hungarian Patent HU 215 563 discloses a device that is adapted for being connected to a vacuum cleaner and has a collector vessel for receiving the removed body fluid.

A number of technical solutions addressing the problems related to the use of the device are included in the prior art.

Such technical solutions are disclosed in Utility Model Nos. HU 3471, HU 3472, and RU 87083 U1, wherein the suction head of the device is connected to the collector vessel, and the device itself consists of releasably interconnected bottom and upper portions that have conical and arcuate configuration.

A common disadvantage of known devices is that the collector vessel of the device is in many cases incapable of retaining the removed body fluid, resulting in that the exudate enters the connection pipe of the vacuum cleaner (or the vacuum cleaner itself) due to the suction effect resulting from the applied vacuum, causing undesirable contamination.

This depends on the consistency of the body fluid being removed.

In recent years, pharmaceutical companies have introduced a number of allegedly antibacterial/medicinal nasal sprays that are capable of loosening and diluting deposited exudates.

After dilution, the body exudate has a water-like consistency, and therefore it cannot be safely removed by applying known devices because the vacuum-generated airflow can carry it off from the collector vessel.

SUMMARY OF THE INVENTION

This invention provides a device that, while preserving the advantageous characteristics of known technical solutions, is capable of safely removing diluted, water-like body fluids.

The device is particularly well suited for removing a body fluid, particularly nasal fluid, by applying a vacuum source, preferably a vacuum cleaner. The device includes a hollow collector vessel having a suction bell and a coacting discharge bell removably connected to the discharge bell. The suction bell has a hollow, conical body which defines a first open end and an air inlet opening opposite the first open end. The discharge bell also has a hollow, conical body which defines a second open end and an air outlet opening opposite the second open end. The first and second open ends are adjacent to one another and together define the hollow collector vessel.

A central member adapted to collect and retain a body fluid is removably held between the suction bell and the discharge bell at their respective open ends and includes an open cup which defines a body fluid receptacle surrounded by an integral apertured disc. The open cup faces the air inlet opening of the suction bell and the apertured disc is held in place at the juncture of the suction bell and the discharge bell.

An elongated, hollow, tapered, torch-shaped member is removably received in the air inlet opening of the suction bell. One end of the torch-shaped member extends into the open cup and the opposite end of the torch-shaped member extends outwardly beyond the air inlet opening and terminates in an open suction cone.

A connecting pipe is centered in the discharge bell at the air outlet opening, is integral with the discharge bell, extends inwardly toward the open cup of the central member and outwardly beyond the air outlet opening.

In a preferred embodiment of the device, the suction bell comprises protrusions at its bottom portion connected to the discharge bell, and the discharge bell comprises seats that are disposed at the upper portion thereof and are adapted for receiving the protrusions of the suction bell.

In a further preferred embodiment of the device according to the invention, the upper portion of the connection pipe situated in the bottom portion of the discharge bell extends towards the central member, the bottom portion thereof extending over the discharge bell and, at its bottom free end, the discharge bell is fitted with protrusions running parallel with the bottom portion of the connection pipe.

In all preferred embodiments of the device according to the invention, the suction bell and the discharge bell have a slightly conical configuration, and the suction bell, the discharge bell, their subcomponents and the central member, as well as the connector members—such as the torch-shaped member fitted with a suction cone—are made of a plastic material such as polyethylene, polypropylene, and the like.

BRIEF DESCRIPTION OF THE DRAWINGS

In the drawings:
FIG. 2 is the sectional view of the central member of the device shown in FIG. 1;
and
FIG. 3 is the top plan view of the central member illustrated in FIG. 1.

DETAILED DESCRIPTION OF THE PREFERRED EMBODIMENTS

Figure 1:
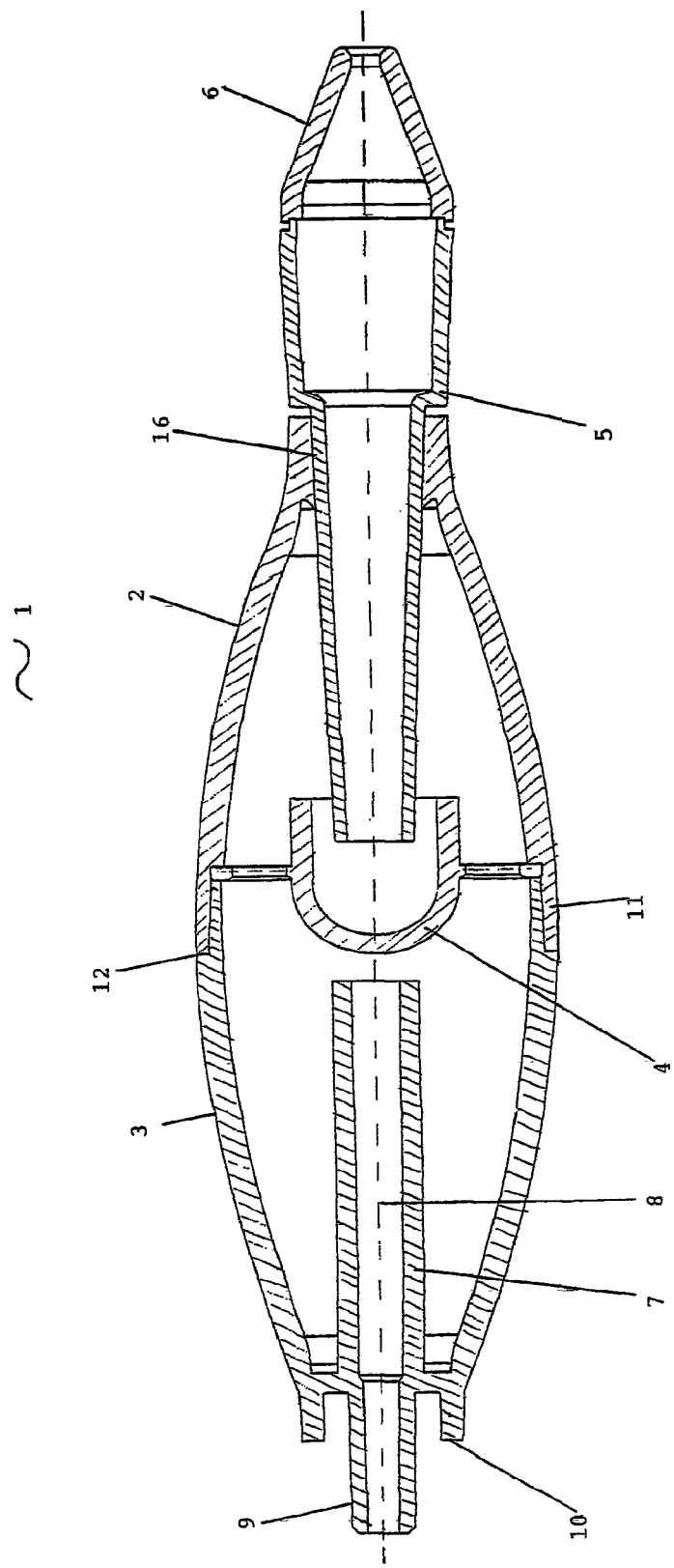
FIG. 1 is a sectional view of the device according to the invention.

Referring to the drawings, device 1 according to the invention is adapted for removing by suction a body fluid, primarily nasal fluid, and can be preferably attached to a vacuum cleaner suction pipe as a suction source.

Device 1 has a releasably interconnected suction bell 2 and discharge bell 3, with central member 4 being held between suction bell 2 and discharge bell 3.

Central member 4 defines receiving member or open cup 14 surrounded by an apertured disc 13 integral or unitary with receiving member or open cup 14. Central member 4 is removably held in place between suction bell 2 and discharge bell 3 by apertured disc 13, the periphery of which is engaged with protrusion 11 of suction bell 2 and seat 12 of discharge bell 3. Apertured disc 13 provides air flow communication between suction bell 2 and discharge bell 3.

Suction bell 2 has a hollow, conical body portion with an open end sized to abut an open end of discharge bell 3. Suction bell 2 also defines air inlet opening 16 opposite its open end. Air inlet opening 16 is sized to removably receive a tapered end portion of torch member 5, the tip of which end portion extends into receiving member or cup 14 removably held between suction bell 2 and discharge bell 3.

Connection pipe 7 coaxial with torch-shaped member 5 is situated in the bottom portion of the discharge bell 3. Upper portion 8 of connection pipe 7 extends towards central member 4 inside discharge bell 3, and forms an end or bottom portion 9 thereof, and extends outwardly beyond discharge bell 3 to provide a connection stub adapted for receiving a connection member for connection to a vacuum source.

Bottom portion of discharge bell 3 is fitted with a protrusion 10 parallel with bottom portion 9 of connection pipe 7 such that, together with bottom portion 9 of connection pipe 7, it forms a seat adapted for receiving the connection member (not shown in the drawings).

FIG. 2 is a sectional view of central member 4 of device 1 shown in FIG. 1 and shows open cup 14 which provides a receiving space for body fluid. Disc 13 surrounds cup 14 and is integral therewith. Disc 13 is provided with apertures or bores 15 having a diameter D (see FIG. 3).

The device according to the invention is operated as follows.

When device 1 is prepared for use, discharge bell 3 and the suction bell 2 are snapped together, holding central member 4 therebetween. To provide a safe connection, protrusion 11 of suction bell 2 is received into seat 12 formed on the upper portion of the discharge bell 3, then suction bell 2 and discharge bell 3 are interconnected by slightly rotating the suction bell 2 along the discharge bell 3.

Protrusion 11 of suction bell 2 and seat 12 of the discharge bell 3 can be configured such that the connection is made solely by protrusion 11 snapping in place in seat 12 during the interconnection of suction bell 2 and discharge bell 3, without performing any further operations.

After that, an end portion of torch-shaped member 5 is received in air inlet opening 16, defined in the upper portion of suction bell 2. The bottom portion of the torch terminates within cup 14 of the central member 4 of the suction bell 2. Removable suction cone 6 is then mounted to the torch-shaped member 5 at the top opening thereof.

The torch-shaped member 5 and suction cone 6 can also be an integral or unitary member, if desired.

A connecting element, i.e., a flexible plastic pipe, is then attached to bottom or end portion 9 of connection pipe 7 in discharge bell 3, with any suitable connection member adapted for facilitating connection of device 1 to a suction pipe of a vacuum cleaner, being disposed at the other end of the connecting element, situated opposite the discharge bell 3.

The device is now ready for removing a body fluid, and can be operated by inserting suction cone 6 into a nostril of a child, and by removing by suction the body fluid by applying the suction produced by the vacuum cleaner.

In operation, an air/body fluid mixture flowing at a relatively high velocity—1.5-2 m/s—is passed via suction cone 6 and torch 5 into cup 14 of central member 4, where the flow direction of the air/body fluid mixture is temporarily reversed and, due to its inertia, the mixture is splashed against the wall of suction bell 2, followed by accumulation at the bottom of the discharge bell 3 while the air portion is carried on unhindered as there is a many thousand fold difference in specific weight between the fluid and air.

Due to the sudden increase of flow diameter, the air flow velocity is significantly reduced—to 1-2 cm/s—so the air flow exiting the device cannot carry off precipitated liquid anymore, even if the liquid gets diluted to a near-water consistency.

Under the influence of vacuum, air is carried further along connection pipe 7 of discharge bell 3 of device 1 that is adapted for preventing fluid from being discharged from the device 1 at any spatial orientation thereof.

Due to its configuration, device 1 can hold approximately 5-6 cm$^3$ of fluid (depending on density) at any given time, which is entirely sufficient for a single instance of removing by suction a body fluid.

After use, the device can be disassembled to its components and can be easily cleaned or, if necessary, sterilized.

The advantage of the device according to the invention is that it can safely remove the fluids accumulated inside the difficult-to-access cavities irrespective of their density. The removed body fluids can be safely retained inside the device, completely preventing them from entering the suction device.

What is claimed is:

1. A device for removing a nasal fluid using a vacuum source which comprises:
    a collector vessel having an outlet and an inlet, and defined by a suction bell, a coacting discharge bell removably connected to the suction bell, and a central member removably held therebetween;
    the suction bell having a hollow, conical body defining a first open end and an air inlet opening opposite the first open end;
    the discharge bell having a hollow, conical body defining a second open end and an air outlet opening opposite the second open end;
    the central member comprising an open cup, defining a receiving space, and surrounded by an integral apertured disc removably held in place between said first and second open ends, the open cup facing said inlet opening;
    an elongated, hollow, tapered, torch-shaped member removably received in said inlet opening, having one end extending into said open cup and an end opposite said one end terminating in an open suction cone extending outwardly away from said inlet opening; and
    a connecting pipe centered in the discharge bell, extending toward said central member and integral with the discharge bell at the outlet opening and extending outwardly therefrom.

2. The device according to claim 1, wherein the receiving space of the central member is a cup open in the direction of the torch-shaped member and closed in the direction of the connection pipe, and the torch-shaped member extends into the receiving space of the central member, while an inner portion of the connection pipe terminates under but spaced from the central member.

3. The device according to claim 1, wherein the suction bell comprises protrusions at a bottom portion connected to the discharge bell, and the discharge bell defines seats that are disposed at an upper portion thereof and are adapted for receiving the protrusions of the suction bell.

4. The device according to claim 1, wherein the discharge bell is fitted with protrusions running parallel to a bottom portion of the connecting pipe.

5. The device according to claim 1, wherein the suction bell, the discharge bell, the central member, the torch-shaped member and the suction cone are made of plastic.

6. The device of claim 1, wherein the open suction cone is removably attached to the torch-shaped member.

* * * * *